United States Patent

Engels

[11] Patent Number: 4,678,609
[45] Date of Patent: Jul. 7, 1987

[54] PROCESS FOR THE PREPARATION OF CORTICOSTEROID-21-PHOSPHORIC ACIDS AND THEIR SALTS AND THE CORTICOSTEROID-21-PHOSPHORIC ACID TRIESTERS

[75] Inventor: Joachim Engels, Kronber, Fed. Rep. of Germany

[73] Assignee: Hoechst Aktiengesellschaft, Fed. Rep. of Germany

[21] Appl. No.: 795,542

[22] Filed: Nov. 6, 1985

[30] Foreign Application Priority Data

Nov. 8, 1984 [DE] Fed. Rep. of Germany ....... 3440794

[51] Int. Cl.$^4$ ............................................. C07J 00/00
[52] U.S. Cl. ............................. 260/397.45; 260/397.4
[58] Field of Search ................. 260/397.45, 239.55 D, 260/397.4

[56] References Cited

U.S. PATENT DOCUMENTS 2,870,177 1/1959 Conbere et al. ................. 260/397.45
3,048,581 8/1962 Fried et al. ................. 260/239.55 D
3,053,834 9/1962 Fried et al. ................. 260/239.55 D Primary Examiner—Leonard Schenkman
Assistant Examiner—Joseph A. Lipovsky
Attorney, Agent, or Firm—Finnegan, Henderson, Farabow, Garrett & Dunner

[57] ABSTRACT

Steroid-21-phosphoric acids and pharmaceutically usable salts thereof of the formula III

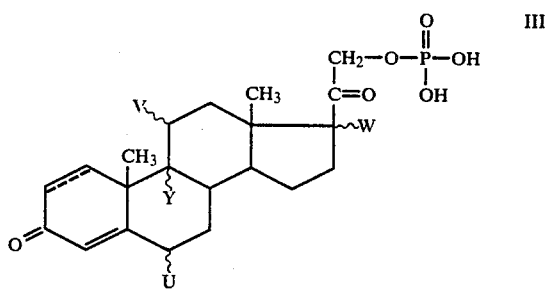

(in which U=H or CH$_3$, V=H, OH, O or Hal; W=H or OH and Y=H or F) are obtained in a very pure state by reacting I

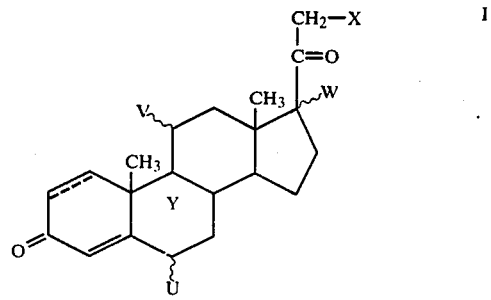

(in which X=OH or Hal) with an organic phosphoric acid ester of the formula IVa or IVb

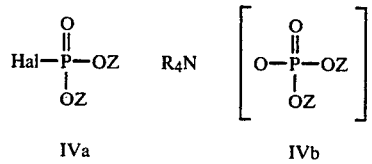

(in which Z=optionally substituted alkyl and R=alkyl). The compounds II

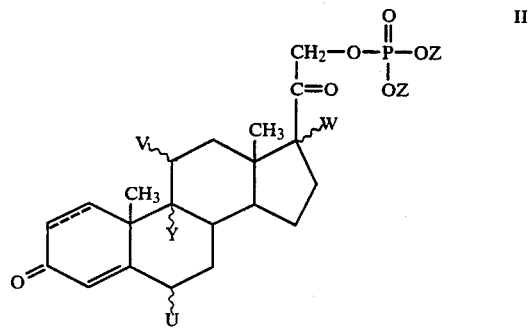

obtained thereby is saponified to give III and the latter, if appropriate, is neutralized to give the salt. Compounds II are new.

4 Claims, No Drawings

PROCESS FOR THE PREPARATION OF CORTICOSTEROID-21-PHOSPHORIC ACIDS AND THEIR SALTS AND THE CORTICOSTEROID-21-PHOSPHORIC ACID TRIESTERS

The present invention relates to a process for the preparation of corticosteroid-21-phosphoric acids and pharmaceutically active salts thereof, in particular methylprednisolone disodium phosphate, and to the corticosteroid-21-phosphoric acid triesters.

Steroid 21-phosphates and pharmaceutically active salts thereof are disclosed in Japanese Published Application No. 41-12,351, U.S. Pat. No. 2,932,657, German Offenlegungsschrift No. 2,225,658 and British Pat. No. 1,010,031. It is a serious disadvantage of the known processes of preparation that, for example, an appreciable proportion of phosphoric acid diester is formed and that, because of the reaction conditions (excess of phosphate), it is very difficult to prepare a steroid phosphate free from extraneous salts.

The object of the invention is, therefore, to prepare corticosteroid-21-phosphoric acids and pharmaceutically active salts thereof in a simple manner and in a highly pure form.

Surprisingly, it has been possible to prepare these compounds of the formula III

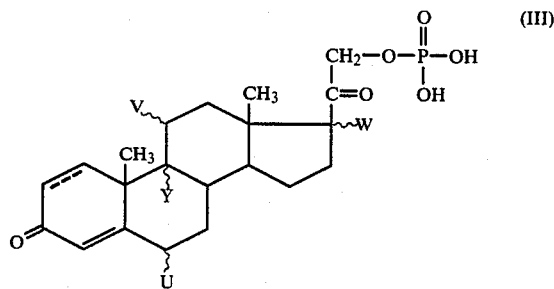

in which
U denotes H or $CH_3$,
V denotes H, OH, O or halogen,
W denotes H or OH and
Y denotes H or F,
or pharmaceutically active salts thereof, by reacting a corticosteroid of the formula I

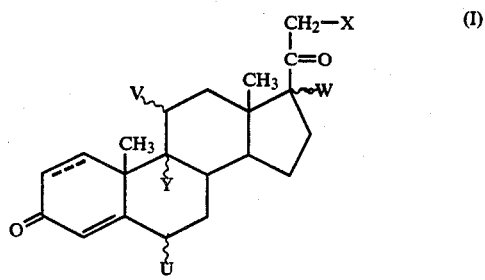

in which
U, V, W and Y have the meaning indicated and
X represents OH or halogen,
with an organic phosphoric acid ester of the formula IVa or IVb

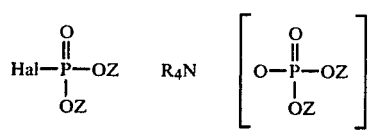

in which
Z is $C_1$–$C_8$-alkyl, preferably $C_1$–$C_4$-alkyl, which can be substituted in the α-position by phenyl which can in turn be substituted by Cl, Br, CN or $NO_2$, it being possible for alkyl radicals having at least 2 carbon atoms to be monosubstituted in the β-position by CN, nitrophenyl or $SO_2$—Cl—4⁻ alkyl or to be disubstituted or trisubstituted by Cl and/or Br, and
Hal is halogen, preferably Cl or Br, and
R denotes $C_1$–$C_8$-alkyl, but one radical R can also be benzyl and/or hydrogen,
and thus preparing a new compound of the formula II

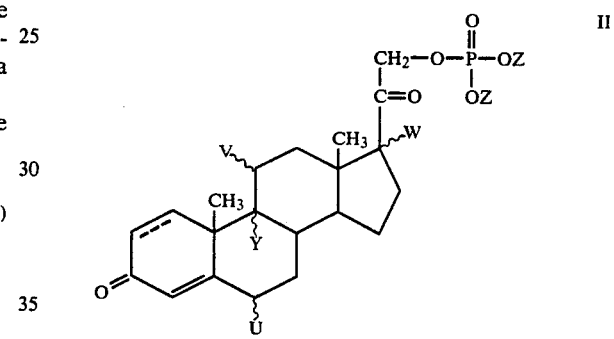

in which
U, V, W, Y and Z have the meanings mentioned, and saponifying this compound II to give the compound III and, if appropriate, neutralizing the latter to give the salt.

If Z contains substituted phenyl radicals, the substituents are preferably in the o-position or p-position.

Processes which have proved particularly suitable for the preparation of the compounds II are those in which a compound of the formula I in which X denotes hydroxyl is reacted with a compound IV in which Hal denotes chlorine. A process in which Z denotes tert.-butyl is also preferred in many cases. A process in which a compound of the formula I in which X=Br or I is reacted with a ($C_1$–$C_8$)-alkylammonium or aralkylammonium salt of a ($C_1$–$C_4$)-dialkylphosphoric acid is also preferred.

The saponification of the compounds II can be effected by means of acids or bases. In many cases it is carried out particularly advantageously by means of acids which have a pK value less than 3, preferably hydrochloric acid or trifluoroacetic acid.

Unless there is an express indication to the contrary, halogen denotes fluorine, chlorine, bromine or iodine.

The process according to the invention embraces, for example, the following embodiments: the reaction of a hydroxycorticosteroid, in particular 6α-methylprednisolone with an organic phosphoric acid diester-chloride, for example ditert.-butylphosphoric acid chloride, in the presence of a base, for example pyridine. Alternatively, 21-iodoprednisolone can be used as the starting material and reacted with an alkylammonium salt of an organic phosphoric acid diester in an inert solvent, such as methylene chloride, acetonitrile or an ether, such as dimethoxyethane. After being extracted into an organic solvent, for example methylene chloride, the resulting corticosteroid-phosphoric acid triester is washed with water and, after the organic phase has been dried, is crystallized out and thus separated from water-soluble impurities and other organic impurities.

In the next stage, the new steroid-phosphoric acid triester II is converted into the corticosteroid-phosphoric acid monoester by means of an acid, for example HCl or trifluoroacetic acid, preferably in an inert solvent, such as chloroform, halogenated hydrocarbons or methylene chloride, at room temperature. The yields decrease at temperatures above 40° C., since the steroid skeleton becomes increasingly unstable. In this process the corticosteroid-phosphate obtained is already in a very good state of purity. The saponification of the steroid-phosphoric acid triester to give the steroid-phosphoric acid monoester can also be carried out under alkaline conditions, if the steroid radical is not alkali-sensitive. After the removal of the solvent and the excess acid, partitioning is carried out between (a) an organic phase, such as, initially, methylene chloride and then, for example, n-butanol or n-hexanol, and (b) water. The pH of the solution is then rendered slightly alkaline in the organic phase by titration with a base, preferably sodium hydroxide solution, and the disodium salt, for example, is thus obtained. In the course of this the disodium salt passes over into the aqueous phase, and the last organic impurities remain in the organic phase.

The resulting steroid 21-phosphate can be obtained in a solid form either by evaporation or by freeze-drying the aqueous solution, if desired after further purification with active charcoal.

Starting corticosteroids of particular interest are cortisol, cortisone, prednisolone, 6α-F-prednisolone, dexamethasone, betamethasone, desoximetasone, 6α-methylprednisolone and the like.

The invention also relates to the new compounds of the formula II obtained in the first stage.

EXAMPLES (1A) 10 g of ditertiary-butylphosphoric acid chloride, dissolved in 30 ml of methylene chloride, were added, at −40° C. and in the course of 20 minutes, to 7.5 g of 6α-methylprednisolone, dissolved in 35 ml of anhydrous pyridine and 8 ml of triethylamine. The reaction was carried out for 40–60 hours at −20° C. After the solvent had been removed, the residue was partitioned between 120 ml of methylene chloride and 40 ml of water. When the organic phase had been washed with water and dried with sodium sulfate, the resulting oil was induced to crystallize by means of ethyl acetate. This gave 7.8 g of the new ditertiary-butyl ester of melting point 153° C. (decomposition)

$[\alpha_D]^{23} = +70.8°$ C,H,P calculated C 63.6 H 8.3 P 5.4% found C 63.2 H 8.3 P 5.2%.

$^{31}$P-NMR (d$_6$DMSO) re. 85% H$_3$PO$_4$ $\epsilon=8.9$ ppm

IR (KBr): $\nu=2980, 2930, 1740, 1650, 1610, 1370, 1260, 1000$ cm$^{-1}$.

$^1$H-NMR: (CDCl$_3$/TMS) $\delta=1.5$ ppm [C-(CH$_3$)$_3$]

(1B) 9.7 g of 21-iodo-6α-methylprednisolone and 15 g of tetra-n-butylammonium bis-tertiary-butyl phosphate were dissolved in 150 ml of acid-free methylene chloride, and the solution was stirred for 20 hours at room temperature. The reaction mixture was then washed with water, a 2% strength thiosulfate solution and then with water and was dried. After the removal of the methylene chloride, the 6α-methylprednisolone-21-phosphoric acid bis-tertiary-butyl ester crystallized from ethyl acetate; 11 g of melting point 150°–152° C. (decomposition). For analytical data see Example 1A.

(1C) 5.3 g of 21-iodo-6α-methylprednisolone and 9 g of benzyltriethylammonium ditertiary-butyl-phosphate were dissolved in 135 ml of dimethoxyethane, and the solution was stirred at room temperature for 40 hours with the exclusion of light. After the solvent had been removed, the residue was partitioned between methylene chloride and water, and the organic phase was washed with thiosulfate and dried with sodium sulfate. The 6 bis-tertiary-butyl α-methylprednisolone-21-phosphoric acid ester was induced to crystallize by means of ethyl acetate, 5.4 g having analytical data identical with those of Example 1A and 1B.

(2) 1.7 g of phosphoric acid dimethyl ester-chloride, dissolved in 25 ml of methylene chloride, were added, at 0° C. and in the course of 30 minutes, to 3.7 g of 6α-methylprednisolone, dissolved in 35 ml of anhydrous pyridine. The reaction was complete after 18 hours at room temperature; the pyridine was removed under reduced pressure. The residue was partitioned between methylene chloride and water (pH 3), and the organic phase was washed with water until neutral and dried with Na$_2$SO$_4$. After the removal of the solvent, the new 6α-methylprednisolone-21-phosphoric acid bis-methylester left as residue (3.1 g) was recrystallized from 8:1 dioxane/dimethylformamide. Melting point 245°–46° C. (decomposition).

$^{31}$P-NMR (d$_6$DMSO) rel. 85% H$_3$PO$_4$ $\delta=2.3$ ppm $^1$H-NMR (d$_6$DMSO) $\delta=3.62$ (doublet) ppm (P-OCH$_3$)

(3) 6.0 g of bis-2,2,2-trichloroethylphosphoric acid chloride were added at room temperature to 3.7 g of 6α-methylprednisolone, dissolved in 42 ml of anhydrous pyridine. The reaction mixture was worked up after 20 hours, the pyridine was removed by distillation under reduced pressure, the residue was partitioned between methylene chloride and water (pH 2), then washed with water until neutral and and the organic phase was dried with Na$_2$SO$_4$. This gave 1.6 g of the new 6α-methylprednisolone-21-phosphoric acid bis-2,2,2-trichloroethylester in the form of colorless crystals of melting point 216°–217° C. $^{31}$P-NMR (d$_6$DMSO) re. 85% H$_3$PO$_4$ $\delta=9.4$ ppm (4) 6.3 g of bis-4-nitrophenylethylphosphoric acid chloride were added at 0° C. to 3.7 g of 6α-methylprednisolone in 40 ml of anhydrous pyridine; the mixture was kept at 0° C. for 2 hours and allowed to stand at room temperature for a further 3 hours. After the removal of the pyridine, the residue was partitioned between methylene chloride and water (pH 3), and the organic phase was rinsed with water and dried with Na$_2$SO$_4$. The crude product was purified by chromatography over 300 g of silica gel, using 3% methanol in methylene chloride as the mobile phase. The new 6α-methylprednisolone-21-phosphoric acid bis-4-nitrophenylethyl ester (5.7 g) crystallized from 4:1 toluene/diethyl ether. Melting point 174°–176° C.

UV (methanol): $\epsilon_{260}=16000$ lxmol$^{-1}$xcm$^{-1}$.

(5) 10.8 g of the ester prepared in accordance with 1A, 1B or 1C were dissolved in 190 ml of chloroform, 10.8 g (7.35 ml) of trifluoroacetic acid were added and the mixture was stirred at room temperature for 20 hours. The solvent and the trifluoroacetic acid were removed under reduced pressure, if necessary with the aid of toluene. The residue was partitioned between distilled water and chloroform and then between water and n-hexanol. The steroid phosphate was then in the n-hexanol. A layer of fresh distilled water was placed below the n-hexanol phase, and the mixture was then titrated carefully with 1 N sodium hydroxide solution to pH 8.6. The aqueous phase was then separated off and washed again with diethyl ether, and the disodium salt of 6α-methylprednisolone-21-phosphoric acid was obtained as a colorless powder by freeze-drying.

$[\alpha_D]^{24} = 84°$ (H$_2$O) $^{31}$P-NMR (D$_2$O) $\delta = 3.5$ ppm

UV: $\epsilon_{243} = 126000$ lxmol$^{-1}$xcm$^{-1}$.

(6) 7.5 g of 6α-methylprednisolone-21-phosphoric acid bis-4-nitrophenylethyl ester according to Example 4 were dissolved at room temperature in 500 ml of diazabicycloundecene in pyridine (0.5 molar), and the mixture was stirred for 40 hours. After the removal of the solvent, the residue was partitioned between methylene chloride and water; the organic extracts were discarded. The pH of the solution was then adjusted to 1 with hydrochloric acid, and the product was extracted into n-butanol or nhexanol. The layer of distilled water was placed under the butanol or hexanol phase, and the mixture was then titrated to pH 8.5 with 1 N NaOH. The aqueous phase was separated off and washed again with diethyl ether, and the disodium salt of 6α-methyl-prednisolone 21-phosphate was obtained as a colorless powder by freeze-drying. It was identical with the product from Example 5.

I claim:

1. A process for the preparation of corticosteroid-21-phosphoric acids of the general formula III

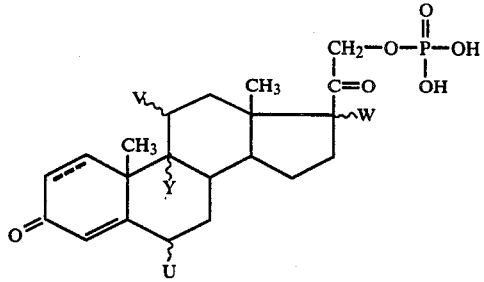

and of pharmaceutically active salts thereof, in which formula III

U denotes H or CH$_3$,

V denotes H, OH, O or halogen,

W denotes H or OH and

Y denotes H or F, which comprises reacting a corticosteroid of the formula I

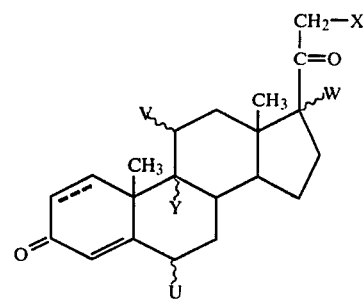

in which U, V, W and Y have the meaning indicated and X represents OH or halogen, with an organic phosphoric acid ester of the formula IVa or IVb

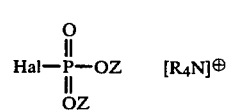 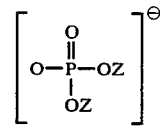

IVa IVb in which

Z is C$_{1-8}$-alkyl which is unsubstituted or substituted in the α-position by phenyl which in turn is unsubstituted or substituted by Cl, Br, CN or NO$_2$, alkyl radicals having at least 2 carbon atoms being unsubstituted or monosubstituted in the β-position by CN, nitrophenyl or SO$_2$—C$_{1-4}$-alkyl or disubstituted or trisubstituted by Cl and/or Br, and Hal denotes halogen and R denotes C$_{1-8}$-alkyl, but a radical R can also be benzyl and/or hydrogen, and thus preparing a compound of the formula II

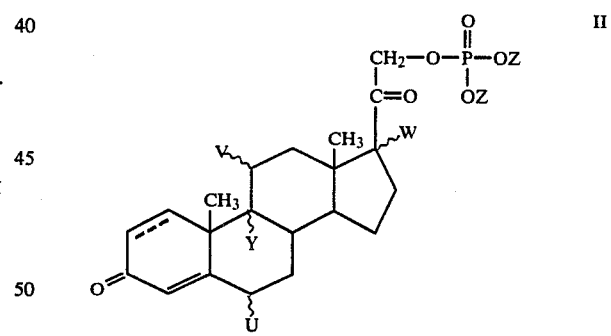

in which U, V, W, Y and Z have the meanings mentioned, and saponifying this compound II to give the compound III and, if appropriate, neutralizing the latter to give the salt.

2. The process as claimed in claim 1, wherein X denotes hydroxyl and Hal denotes chlorine.

3. The process as claimed in claim 1, wherein X denotes bromine or iodine and wherein the compound of the formula I is reacted with a (C$_1$-C$_8$)-alkylammonium or aralkylammonium salt of a (C$_1$-C$_4$)-dialkylphosphoric acid.

4. The process as claimed in claim 1, wherein the saponification is carried out by means of an acid having a phK value of less than 3.

* * * * *